United States Patent
Takahashi et al.

(10) Patent No.: US 7,340,352 B2
(45) Date of Patent: Mar. 4, 2008

(54) INSPECTING METHOD, INSPECTING APPARATUS, AND METHOD OF MANUFACTURING SEMICONDUCTOR DEVICE

(75) Inventors: Naohiro Takahashi, Kawasaki (JP); Kiyoshi Irino, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 11/588,319

(22) Filed: Oct. 27, 2006

(65) Prior Publication Data

US 2007/0255513 A1    Nov. 1, 2007

(30) Foreign Application Priority Data

Apr. 27, 2006  (JP)  ................ 2006-123545

(51) Int. Cl.
*G01B 5/28*  (2006.01)
*G06F 19/00*  (2006.01)

(52) U.S. Cl. .......................... 702/35; 702/83
(58) Field of Classification Search ............ 702/83, 702/35

See application file for complete search history.

(56) References Cited

U.S. PATENT DOCUMENTS

| | | | |
|---|---|---|---|
| 2002/0113234 A1* | 8/2002 | Okuda et al. ............... | 257/48 |
| 2005/0102591 A1* | 5/2005 | Matsushita et al. ........ | 714/724 |
| 2005/0168731 A1* | 8/2005 | Shibuya et al. ............ | 356/237.4 |

FOREIGN PATENT DOCUMENTS

| | | |
|---|---|---|
| JP | 11-219997 A | 8/1999 |
| JP | 2004-263391 A | 9/2004 |
| JP | 2006-105946 A | 4/2006 |

* cited by examiner

*Primary Examiner*—Michael P. Nghiem
*Assistant Examiner*—Cindy D. Khuu
(74) *Attorney, Agent, or Firm*—Westerman, Hattori, Daniels & Adrian, LLP.

(57) ABSTRACT

An inspecting method is capable of efficiently inspecting a wafer. According to the inspecting method, the chip area of a wafer is inspected for defects, and based on the results, a defect density $D_{Op}$ of each of peripheral-zone chips in the chip area which are located closely to the peripheral area of the wafer is calculated. A peripheral-zone chip with a high defect density $D_{Op}$ is selected, and an area in the peripheral area which is outward of the selected peripheral-zone chip is inspected for defects. Since only the area in the peripheral area which is located outward of the peripheral-zone chip selected based on the defect density $D_{Op}$ is inspected for defects, the wafer is inspected efficiently.

18 Claims, 9 Drawing Sheets

INSPECTING METHOD, INSPECTING APPARATUS, AND METHOD OF MANUFACTURING SEMICONDUCTOR DEVICE

CROSS-REFERENCE TO RELATED APPLICATIONS

This application is based upon and claims the benefits of priority from the prior Japanese Patent Application No. 2006-123545, filed on Apr. 27, 2006, the entire contents of which are incorporated herein by reference.

BACKGROUND OF THE INVENTION (1) Field of the Invention

The present invention relates to an inspecting method, an inspecting apparatus, and a method of manufacturing a semiconductor device, and more particularly to a method of and an apparatus for inspecting a wafer for a pattern defect, a foreign matter deposition, or the like, and a method of manufacturing a semiconductor device, which includes such an inspecting process.

(2) Description of the Related Art

In the process of manufacturing semiconductor devices, inspecting apparatus including an appearance inspecting apparatus, a surface foreign matter inspecting apparatus, etc. are used to inspect wafers for pattern defects, foreign matter depositions, or the like (hereinafter referred to as "defect"). For determining the cause of a defect, it has been customary to detect the positional coordinate of the defect on a wafer or confirm the shape of the defect, the size of the defect, etc. with a scanning electron microscope (SEM).

According to the conventional inspecting process, chip areas (hereinafter referred to as "effective chip area) on wafers where chips to be used as products are formed are selectively inspected. An effective chip area usually contains many patterns of devices and interconnections. Though a defect such as a pattern peel, a particle deposition, or the like is found in the effective chip area by the inspecting process, the information of the defect is not sufficient to specify the source of the defect or determine the cause of the defect.

A detailed inspection of a wafer with an SEM often reveals the source of a defect found in a peripheral wafer area outward of the effective chip area. In order to determine the source of a defect for optimizing the process conditions and performing maintenance of the semiconductor device fabrication apparatus for an increased chip yield, growing importance has recently been attached to the inspection of peripheral wafer areas (see, for example, Japanese Unexamined Patent Publication No. 2006-105946).

Of the chips on a wafer, i.e., of the chips in the effective chip area of the wafer, those chips which are positioned in a peripheral zone of the effective chip area are more likely to suffer defects. In view of this tendency, there has heretofore been proposed an inspection system for inspecting chips in greater detail in the peripheral zone of the effective chip area of a wafer than in a central zone thereof and for shortening the period of time required to inspect the wafer (see, for example, Japanese laid-open patent publication No. 11-219997).

If the peripheral wafer area outward of the effective chip area of a wafer, as well as the effective chip area thereof, is to be inspected for greater wafer inspection reliability, then the amount of data processed by the inspecting apparatus is so large and the period of time required to inspect the wafer is so long that the throughput of the semiconductor device fabrication process is low.

Inspecting apparatus or inspecting systems that are not designed to inspect the peripheral wafer area outward of the effective chip area of a wafer are incapable of automatically inspecting the peripheral wafer area in the same manner as they inspect the effective chip area. It will take a large expenditure of time and labor to inspect both the effective chip area and the peripheral wafer area with those inspecting apparatus or inspecting systems.

SUMMARY OF THE INVENTION

It is an object of the present invention to provide a method of and an apparatus for efficiently inspecting both a chip area and a peripheral area outward of the chip area on a wafer.

Another object of the present invention to provide a method of manufacturing a semiconductor device efficiently with a high yield through inspecting a chip area and a peripheral area outward of the chip area on a wafer.

To achieve the first-mentioned object, there is provided a method of inspecting a wafer for defects, the wafer having a chip area and a peripheral area outward of the chip area, the method comprising the steps of performing a first defect inspection on the chip area, calculating defect densities of peripheral-zone chips in the chip area which are close to the peripheral area, based on the first defect inspection, selecting one of the peripheral-zone chips based on the calculated defect density, and performing a second defect inspection on an area in the peripheral area which is positioned outward of the selected peripheral-zone chip.

To achieve the first-mentioned object, there is also provided an apparatus for inspecting a wafer for defects, the wafer having a chip area and a peripheral area outward of the chip area, the apparatus comprising first inspecting means for performing a first defect inspection on the chip area, calculating means for calculating defect densities of peripheral-zone chips in the chip area which are close to the peripheral area, based on the first defect inspection, selecting means for selecting one of the peripheral-zone chips based on the calculated defect density, and second inspecting means for performing a second defect inspection on an area in the peripheral area which is positioned outward of the selected peripheral-zone chip.

To achieve the other object, there is provided a method of manufacturing a semiconductor device from a wafer having a chip area and a peripheral area outward of the chip area, the method comprising the steps of performing a first defect inspection on the chip area, calculating defect densities of peripheral-zone chips in the chip area which are close to the peripheral area, based on the first defect inspection, selecting one of the peripheral-zone chips based on the calculated defect density, and performing a second defect inspection on an area in the peripheral area which is positioned outward of the selected peripheral-zone chip.

The above and other objects, features, and advantages of the present invention will become apparent from the following description when taken in conjunction with the accompanying drawings which illustrate preferred embodiments of the present invention by way of example.

DESCRIPTION OF THE PREFERRED EMBODIMENTS

Embodiments of the present invention will be described in detail below with reference to the drawings.

First, the principles of a process of inspecting a wafer will be described below.

Figure 1:
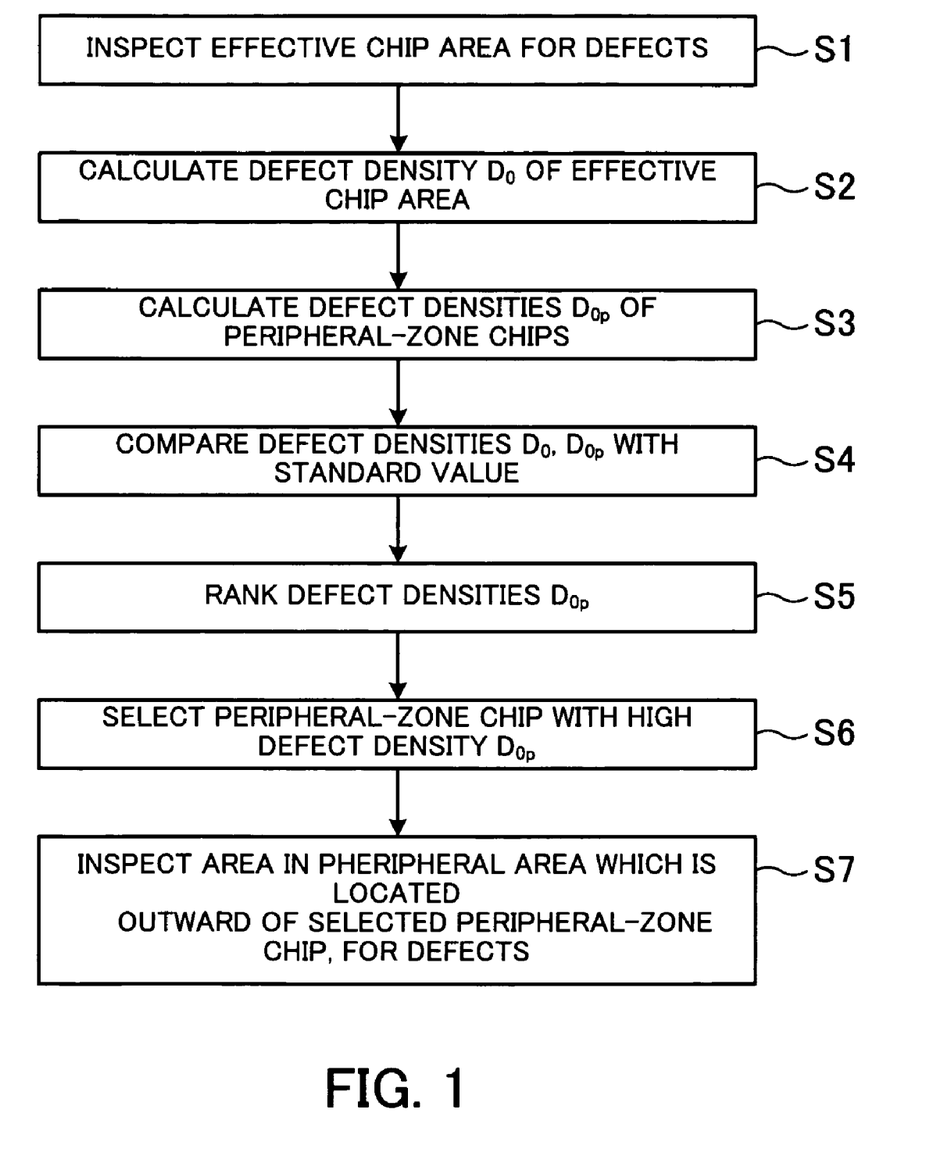
FIG. 1 is a flowchart of a process of inspecting a wafer.
Figure 2:
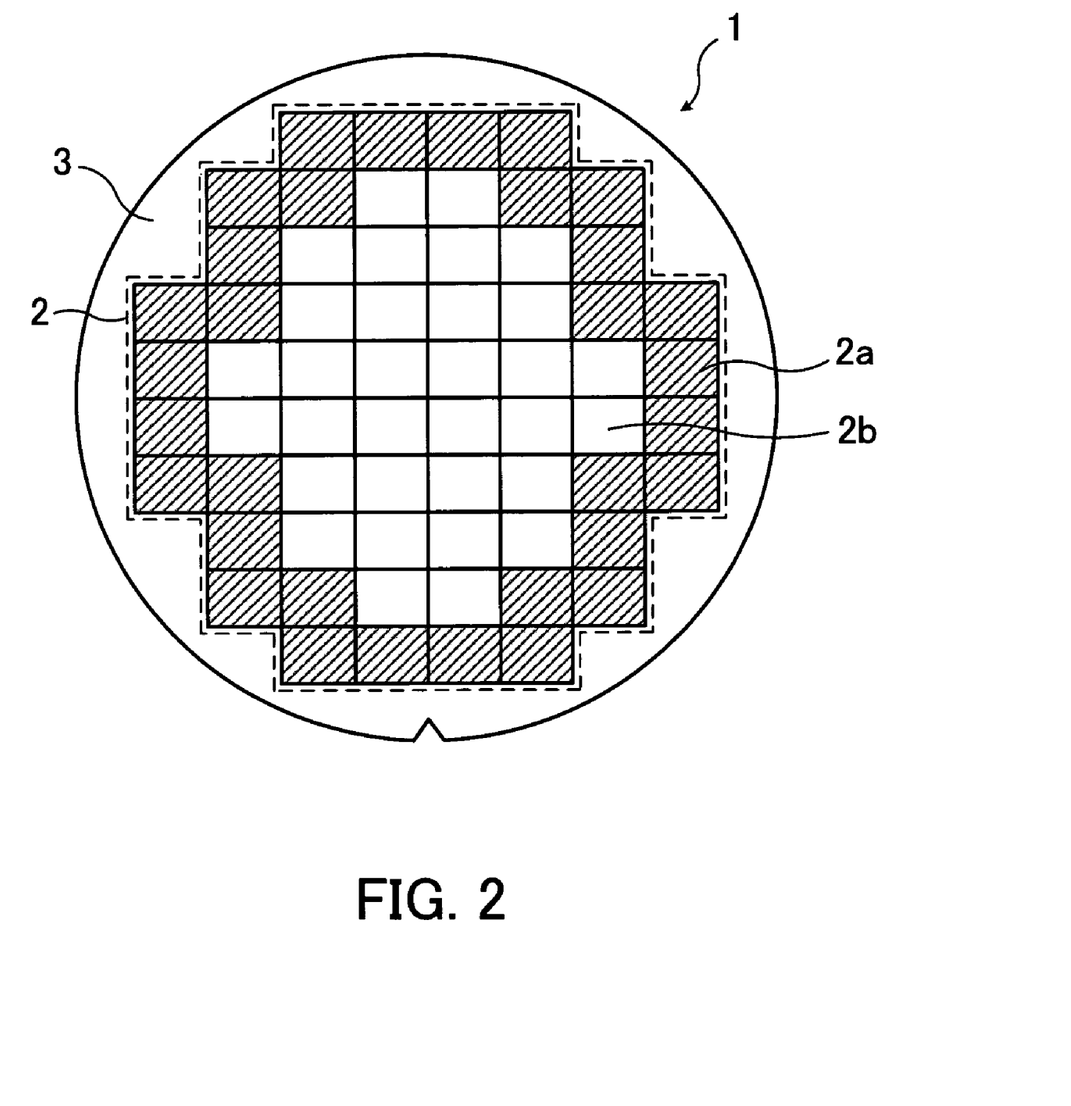
FIG. 2 is a plan view of a wafer.

FIG. 2 shows a wafer 1 in plan.

As shown in FIG. 2, the wafer 1 has an effective chip area 2 where a number of chips, which may be completed or may be being processed, are disposed, and a peripheral area 3 outward of the effective chip area 2. The chips disposed in the effective chip area 2 are classified into chips 2a (hereinafter referred to as "peripheral-zone chips 2a") that are positioned in a zone close to the peripheral area 3, and chips 2b (hereinafter referred to as "central chips 2b") that are positioned radially inwardly from the peripheral-zone chips 2a.

Figure 3:
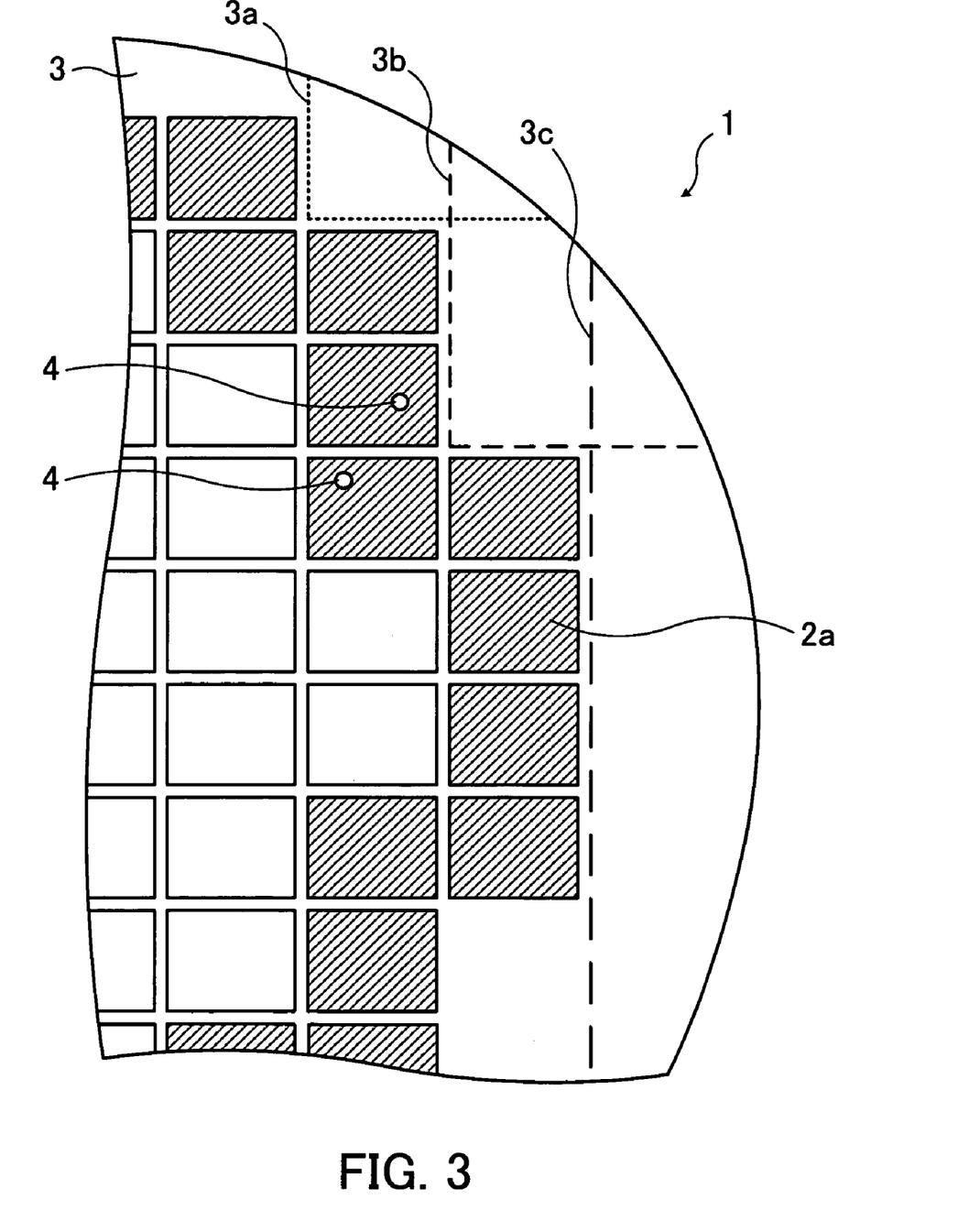
FIG. 3 is an enlarged fragmentary plan view of a peripheral area of the wafer before it is inspected for defects.

FIG. 3 shows a process of inspecting a wafer.

For inspecting the wafer 1 according to the inspecting process shown in FIG. 3, an inspecting apparatus first performs a defect inspection (first defect inspection) on only the effective chip area 2 (step S1).

The inspecting apparatus may be an appearance inspecting apparatus, a laser-beam surface foreign matter inspecting apparatus, or the like. Inspection result data produced by the inspecting apparatus include a product number, a lot, the ID and size (diameter) of the wafer 1, information about the inspecting apparatus, the inspection date, the coordinates of each of the chips, including the peripheral-zone chips 2a and the central chips 2b, on the wafer 1, the size of each of the chips, the number of defects, the coordinates of the defects, the sizes of the defects, etc.

Then, using the inspection result data obtained with respect to the effective chip area 2, a defect density $D_0$ of the entire effective chip area 2 is calculated (step S2). Thereafter, a defect density $D_{Op}$ of each of the peripheral-zone chips 2a in the effective chip area 2 is calculated (step S3).

After the defect densities $D_0$, $D_{Op}$ are calculated, their values are compared with a predetermined standard defect density value (step S4). Specifically, it is determined whether the defect densities $D_0$, $D_{Op}$ satisfy the relationship: standard defect density value<$D_0$<$D_{Op}$ or not. If the relationship is satisfied, then non-standard defects are included in the effective chip area 2, and particularly many defects are included in the peripheral-zone chips 2a.

With respect to a wafer 1 that has not been up to given standards, the defect densities $D_{Op}$ calculated for the respective peripheral-zone chips 2a are ranked (step S5).

Thereafter, peripheral-zone chips 2a having high defect densities $D_{Op}$ are selected (step S6). For example, one or more peripheral-zone chips 2a whose defect densities $D_{Op}$ are higher than a preset constant value are selected, or a predetermined number of peripheral-zone chips 2a having higher defect densities $D_{Op}$ are selected, or only a peripheral-zone chip 2a with the highest defect density $D_{Op}$ is selected. The constant value used as a criterion for selecting peripheral-zone chips 2a may be established depending on the configuration, use, or required characteristics of the chips.

After certain peripheral-zone chips 2a have been selected, the inspecting apparatus performs a defect inspection (second defect inspection) on an area in the peripheral area 3 which is disposed outward of the selected peripheral-zone chips 2a, i.e., disposed closely to the outer circumferential edge of the wafer 1 (step S7). Details of the defect inspection on the peripheral area 3 outward of the selected peripheral-zone chips 2a will be described later.

According to the above wafer inspecting process, after the effective chip area 2 is inspected for defects, peripheral-zone chips 2a in the effective chip area 2 which are positioned closely to the peripheral area 3 and have higher defect densities $D_{Op}$ are selected, and then the peripheral area 3 outward of the selected peripheral-zone chips 2a is inspected for defects.

If many defects are present in the peripheral area 3 or a large defect is present in the peripheral area 3, then the many defects or the large defect tends to serve as a source of defects in the effective chip area 2, i.e., tends to be scattered to chips near the peripheral area 3, i.e., peripheral-zone chips 2a, in particular, causing defect densities $D_{Op}$ thereof to be higher.

The above wafer inspecting process is capable of selectively inspecting an area that needs to be inspected for defects, in the peripheral area 3. Consequently, the wafer 1 is inspected more efficiently than if the peripheral area 3 is inspected in its entirety.

Based on the information obtained from the above wafer inspecting process, the source of defects and the cause of defects are determined thereby to discover the cause of a reduction in the yield. After a semiconductor device fabrication apparatus for manufacturing the wafer 1, which has suffered the reduction in the yield, has been repaired, wafers processed by the repaired semiconductor device fabrication apparatus are inspected by the above wafer inspecting process. Based on the results of the wafer inspecting process, it is possible to confirm efficiently whether the repaired semiconductor device fabrication apparatus is operating normally or the semiconductor device fabrication apparatus has been repaired properly.

Furthermore, since the wafer 1 is inspected efficiently, the period of time required to inspect the wafer 1 is shortened, and the throughput of a semiconductor device fabrication process including the wafer inspecting process is increased. The results of the wafer inspecting process which is made efficient can quickly be fed back to the semiconductor device fabrication process.

The inspecting process carried out in step S7 will be described in detail below.

For inspecting the peripheral area 3 outward of the peripheral-zone chips 2a selected based on the defect densities $D_{Op}$, a limited area is established as an inspection area in the peripheral area 3, and only the established limited area is inspected.

Figure 4:
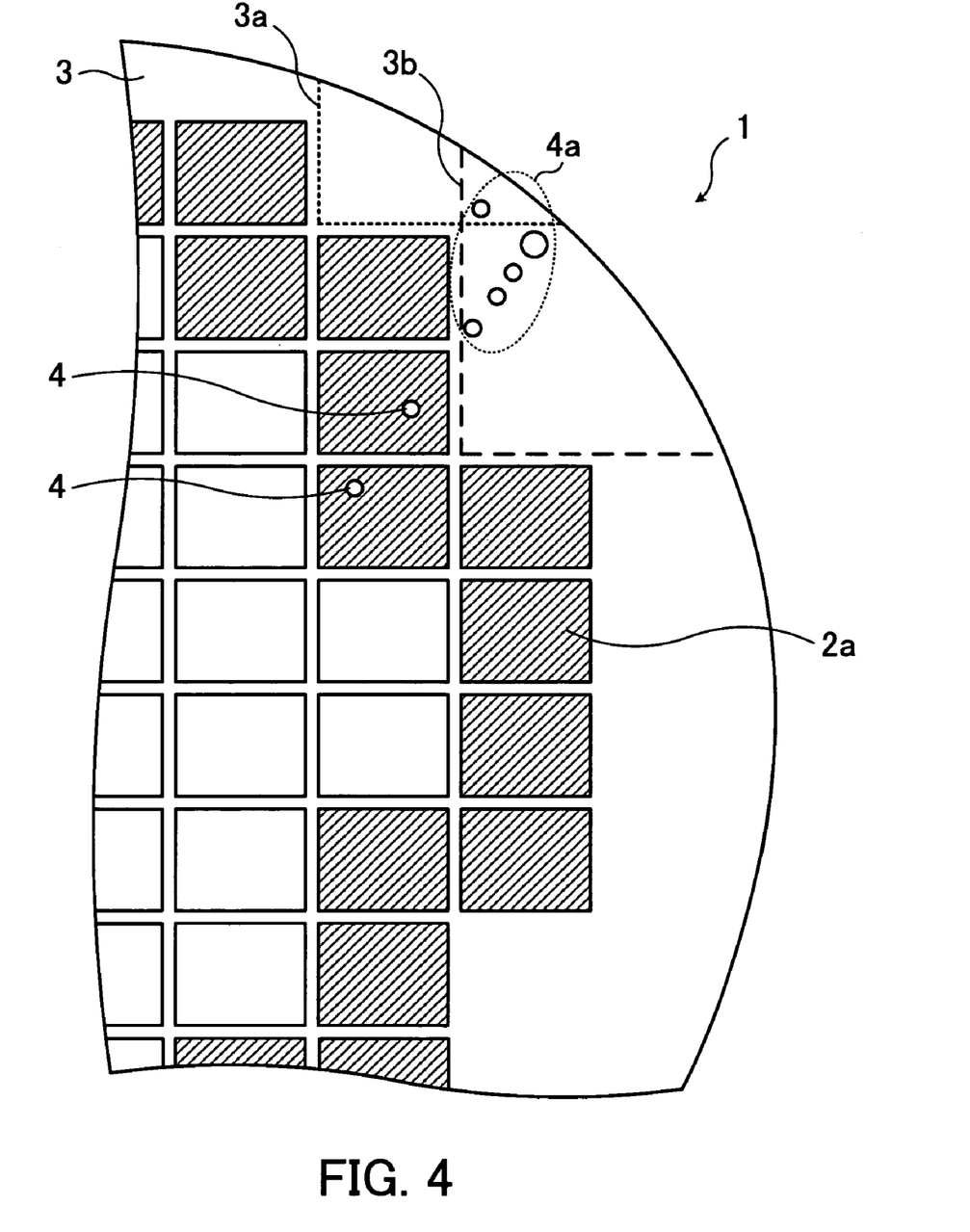
FIG. 4 is an enlarged fragmentary plan view of the peripheral area of the wafer after it is inspected for defects.

FIG. 3 is an enlarged fragmentary plan view of a peripheral area of the wafer before it is inspected for defects, and FIG. 4 is an enlarged fragmentary plan view of the peripheral area of the wafer after it is inspected for defects.

As shown in FIG. 3, sectorial areas 3a, 3b and an arcuate area 3c are preset as inspection areas in the peripheral area 3. Of these inspection areas, an area or areas disposed outward of the peripheral-zone chips 2a selected based on the defect densities $D_{Op}$, or an area or areas close thereto are inspected for defects.

The sectorial areas 3a, 3b and the arcuate area 3c are preset in a region extending from the edges of the peripheral-zone chips 2a to the outer circumferential edge of the wafer 1 so as not to overlap the peripheral-zone chips 2a. Specifically, the sectorial areas 3a, 3b and the arcuate area 3c are preset such that they do not overlap the peripheral-zone chips 2a and portions of the outer circumferential edge of the wafer 1 serve as arcuate edges of the sectorial areas 3a, 3b and the arcuate area 3c. The inspection areas thus preset may overlap each other. The inspection areas may be preset by dividing the entire peripheral area 3 into sectorial and arcuate areas outward of the peripheral-zone chips 2a, using the positional coordinates of the effective chip area 2 on the wafer 1 and the positional coordinates of the peripheral-zone chips 2a in the effective chip area 2 on the wafer 1. The inspection areas are preset on the inspecting apparatus which has been used to inspect the effective chip area 2 for defects, for example.

In the example shown in FIG. 3, a peripheral-zone chip 2a containing a defect 4 is selected based on the defect densities $D_{Op}$. Thereafter, an inspection area located immediately next to and just outward of the selected peripheral-zone chip 2a, i.e. the sectorial area 3b, is selected, and inspected for defects.

As shown in FIG. 4, defects 4a that are present in the sectorial area 3b are detected. Consequently, the defects 4a that are present in the sectorial area 3b can efficiently be detected.

If some of the defects 4a that are present in the sectorial area 3b are present in an overlapping zone of the sectorial areas 3a, 3b, then the sectorial area 3a is also inspected for defects. Since not only the sectorial area 3b located immediately next to and just outward of the peripheral-zone chips 2a selected based on the defect densities $D_{Op}$, but also the nearby sectorial area 3a containing a defect 4a are inspected for defects, detailed information about the defects 4, 4a, representing a distribution of the defects 4, 4a on the wafer, etc., can be obtained.

The inspection areas preset in the peripheral area 3 are illustrated as being of sectorial and arcuate shapes. However, even by setting the inspection areas other shapes, similar operation and effects can be obtained.

Figure 5:
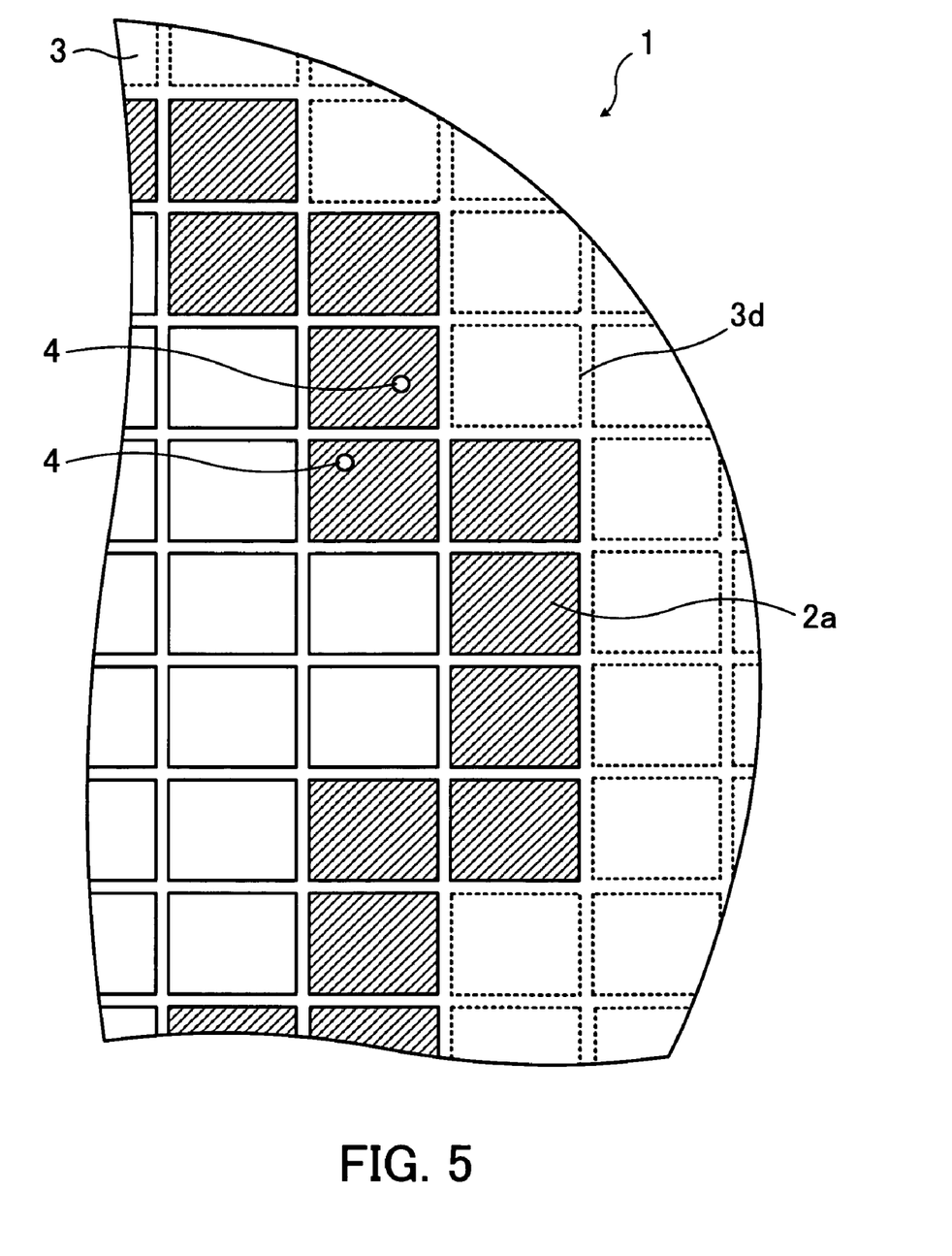
FIG. 5 is an enlarged fragmentary plan view of a peripheral area of another wafer before it is inspected for defects.
Figure 6:
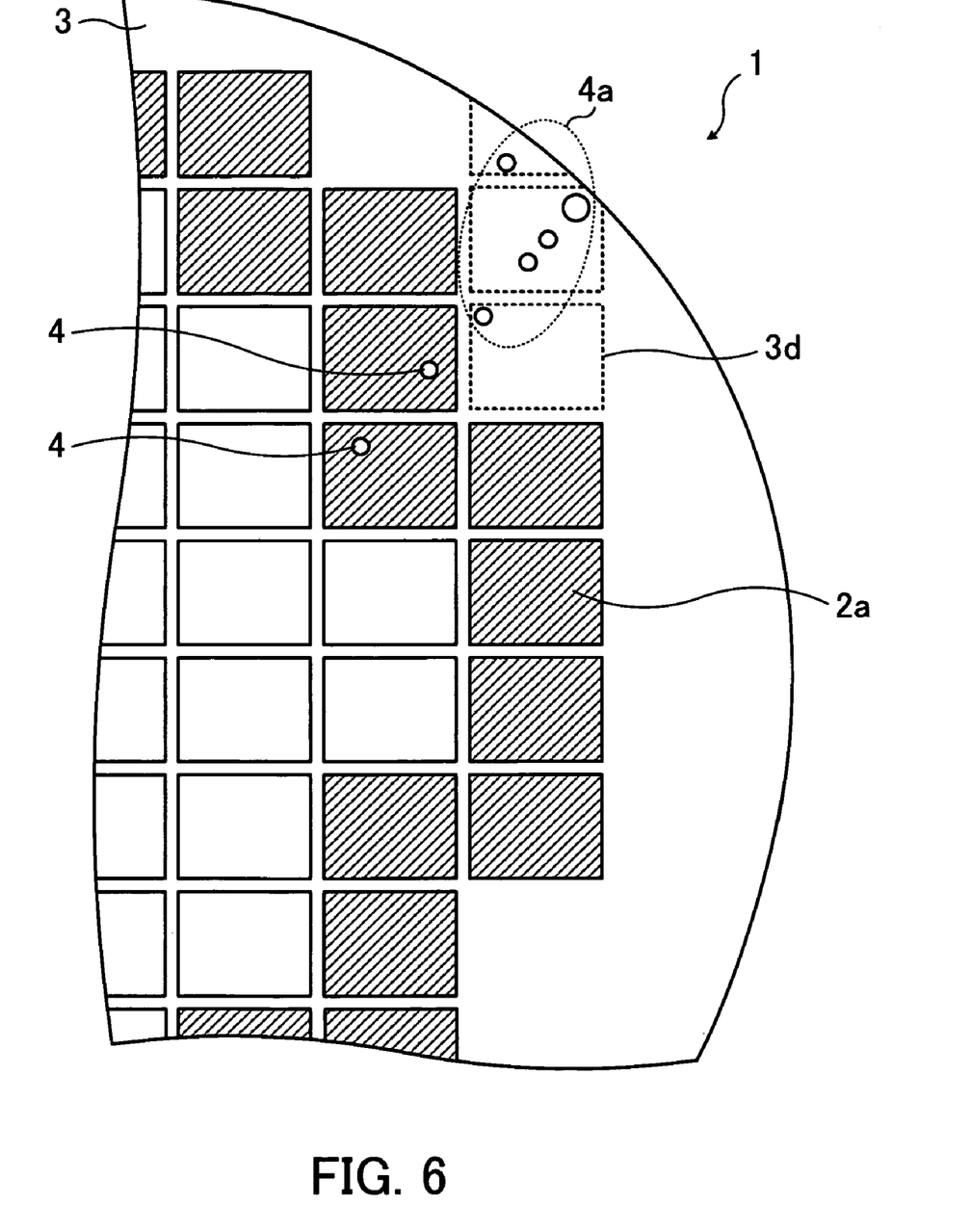
FIG. 6 is an enlarged fragmentary plan view of the peripheral area of the other wafer after it is inspected for defects.

FIG. 5 is an enlarged fragmentary plan view of a peripheral area of another wafer before it is inspected for defects, and FIG. 6 is an enlarged fragmentary plan view of the peripheral area of the other wafer after it is inspected for defects.

In FIG. 5, inspection areas preset in the peripheral area 3 are in the form of a plurality of hypothetical chips 3d which are identical in shape and size to the peripheral-zone chips 2a. The inspection areas may be preset by arranging hypothetical chips 3d in the entire peripheral area 3 in the same pattern as the peripheral-zone chips 2a and the central chips 2b in the effective chip area 2, using the positional coordinates of the peripheral-zone chips 2a and the central chips 2b on the wafer 1. The inspection areas are preset on the inspecting apparatus which has been used to inspect the effective chip area 2 for defects, for example.

In the example shown in FIG. 5, a peripheral-zone chip 2a containing a defect 4 is selected based on the defect densities $D_{Op}$. Thereafter, a hypothetical chip 3d close to the selected peripheral-zone chip 2a is selected. Specifically, a hypothetical chip 3d immediately next to the selected peripheral-zone chip 2 selected based on the defect densities $D_{Op}$, or such a hypothetical chip 3d and one or more hypothetical chips 3d close thereto are selected.

As shown in FIG. 6, defects 4a that are present in hypothetical chips 3d are detected. As a result, defects 4a that are present in the peripheral area 3 can efficiently be detected.

If a plurality of hypothetical chips 3d are to be selected as inspection areas, then the range in which hypothetical chips 3d are to be selected and the number of hypothetical chips 3d are to be selected may be appropriately established based on a hypothetical chip 3d immediately next to the peripheral-zone chip 2a selected based on the defect densities $D_{Op}$. As the number of hypothetical chips 3d to be selected is greater, more detailed information can be obtained with respect to defects 4 that are present in a wider range in the peripheral area 3, and hence the reliability of the wafer inspecting process is higher. However, it should be noted that as the number of hypothetical chips 3d to be selected is increased, the amount of data handled in the wafer inspecting process and the time required to perform the wafer inspecting process are increased.

The above wafer inspecting process may be performed by an inspecting apparatus such as an appearance inspecting apparatus, a laser-beam surface foreign matter inspecting apparatus, or the like. The inspecting apparatus has an inspecting mechanism and a computer for controlling the inspecting mechanism and processing inspection data. The inspecting apparatus also has a software program and performs a predetermined inspection processing sequence according to the algorithm of the software program. The inspection processing sequence performed by the inspecting apparatus will be described below.

Figure 7:
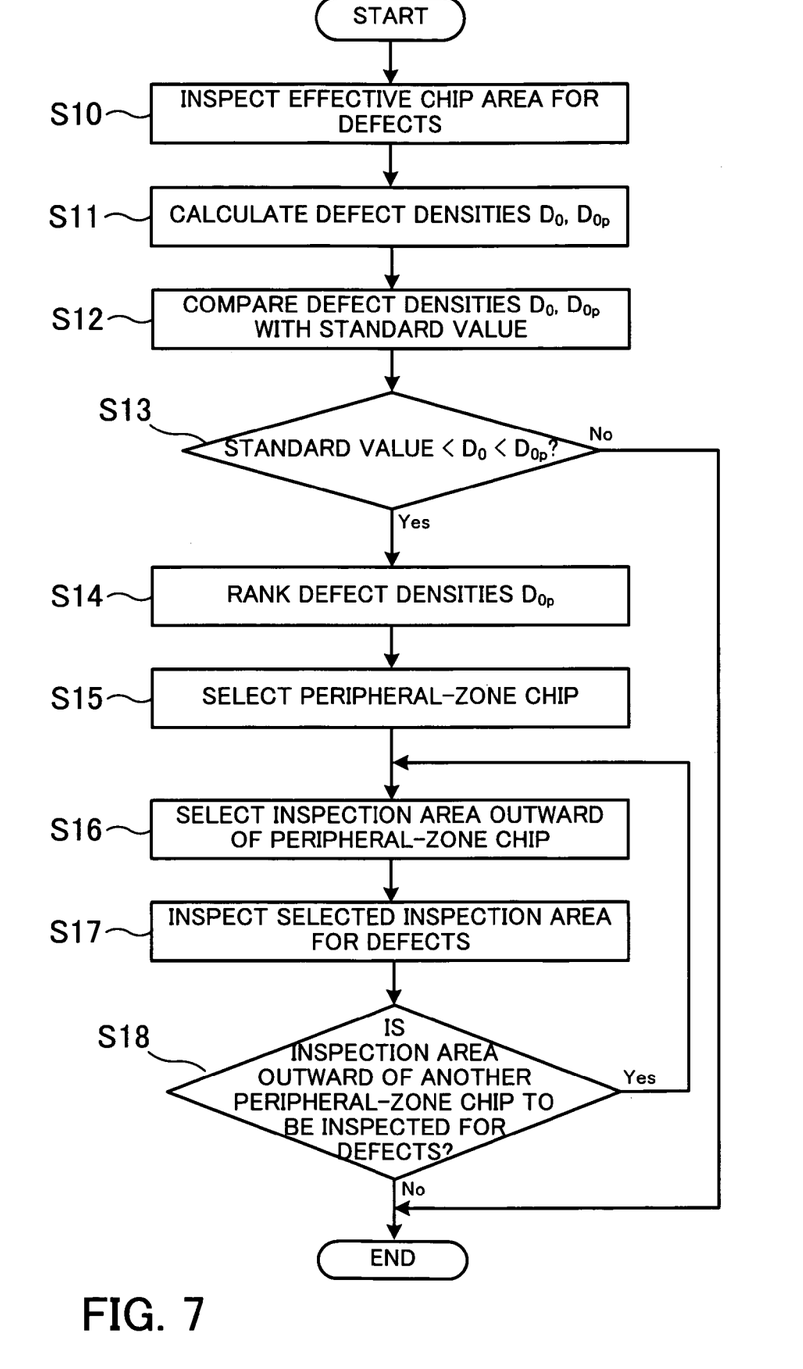
FIG. 7 is a flowchart of a processing sequence of an inspecting apparatus.

FIG. 7 is a flowchart of the inspection processing sequence of the inspecting apparatus.

The inspecting apparatus inspects the effective chip area 2 on the wafer 1 for defects (step S10). Thereafter, the inspecting apparatus calculates a defect density $D_0$ of the entire effective chip area 2 and a defect density $D_{Op}$ of each of the peripheral-zone chips 2a in the effective chip area 2 based on the data of the inspection result (step S11).

After having calculated the defect densities $D_0$, $D_{Op}$, the inspecting apparatus compares the calculated defect densities $D_0$, $D_{Op}$ a preset standard defect density value (step S12), and determines whether the relationship: standard defect density value$<D_0<D_{Op}$ is satisfied therebetween or not (step S13).

If the relationship: standard defect density value$<D_0<D_{Op}$ is satisfied in step S13, then the inspecting apparatus determines that the wafer 1 is not up to given standards, and many defects are present in the peripheral-zone chips 2a in particular. The inspecting apparatus ranks the defect densities $D_{Op}$ calculated with respect to the respective peripheral-zone chips 2a (step S14).

Based on the ranked defect densities $D_{Op}$, the inspecting apparatus selects one or more peripheral-zone chips 2a having higher defect densities $D_{Op}$ (step S15). At this time, the inspecting apparatus may select, as described above, one or more peripheral-zone chips 2a whose defect densities $D_{Op}$ are higher than a preset constant value are selected, or a predetermined number of peripheral-zone chips 2a having higher defect densities $D_{Op}$, or only a peripheral-zone chip 2a with the highest defect density $D_{Op}$.

After having selected a peripheral-zone chip 2a or peripheral-zone chips 2a, the inspecting apparatus selects an inspection area outward of the selected peripheral-zone chip 2a or each of the selected peripheral-zone chips 2a (step S16). For example, the inspecting apparatus selects a sectorial or arcuate inspection area (see FIGS. 3 and 4) in the peripheral area 3 or an inspection area from an array of hypothetical chips, identical in shape and size to the peripheral-zone chips 2a, in the peripheral area 3 (see FIGS. 5 and 6).

The inspection areas are established in advance by the inspecting apparatus in the entire peripheral area 3 outward of the effective chip area 2, using the positional coordinates of the effective chip area 2 on the wafer 1 and the positional coordinates of the peripheral-zone chips 2a and the central chips 2b in the effective chip area 2 on the wafer 1. The inspecting apparatus selects a peripheral-zone chip 2a which satisfies certain conditions and selects an inspection area positioned outward of the selected peripheral-zone chip 2a from the inspection areas established in the entire peripheral area 3.

After having selected the inspection area, the inspecting apparatus inspects the selected inspection area outward of the selected peripheral-zone chip 2a for defects (step S17).

After the inspection of the selected inspection area for defects in step S17, the inspecting apparatus determines whether an inspection area outward of another peripheral-zone chip 2a is to be inspected for defects or not (step S18). When a plurality of peripheral-zone chips 2a is selected in step S15, the inspecting apparatus determines in the present cycle in step S18 that an inspection area outward of another peripheral-zone chip 2a is to be inspected for defects. Thereafter, control goes back to step S16. The processing of steps S16, S17 is repeated with respect to all peripheral-zone chips 2a selected in step S15.

If the relationship: standard defect density value<$D_0$<$D_{0p}$ is not satisfied in step S13, then the inspecting apparatus determines that the wafer 1 is up to the given standards, and finishes its processing sequence on the wafer 1.

When the inspecting apparatus performs the above processing sequence, it inspects the wafer 1 reliably and efficiently. The inspecting apparatus inspects a given inspection area outward of a peripheral-zone chip 2a that satisfies certain conditions, and sends the results of the inspection to an appropriate fabrication process through a feedback loop for thereby contributing to an increase in the chip yield.

The data of the inspection results acquired with respect to the peripheral area 3 are processed in relation to the data of the results of the inspection performed on the effective chip area 2. For example, the data are stored in a storage device such as an HDD (Hard Disk Drive) or the like of the inspecting apparatus, and read therefrom when necessary for a DSA (Defect Source Analysis), an FIB (Focused Ion Beam) section analysis, etc., of the fabrication process.

The above wafer inspecting process as it is applied to a semiconductor device fabrication process will be described below.

Specifically, the wafer inspecting process as it is applied to a MOS transistor fabrication process will be described below. A MOS transistor has its basic structure produced by a device separation area forming process, a well area forming process, a gate insulating film forming process, a gate electrode forming process, and a source/drain area forming process which are performed on a semiconductor substrate.

Figure 8:
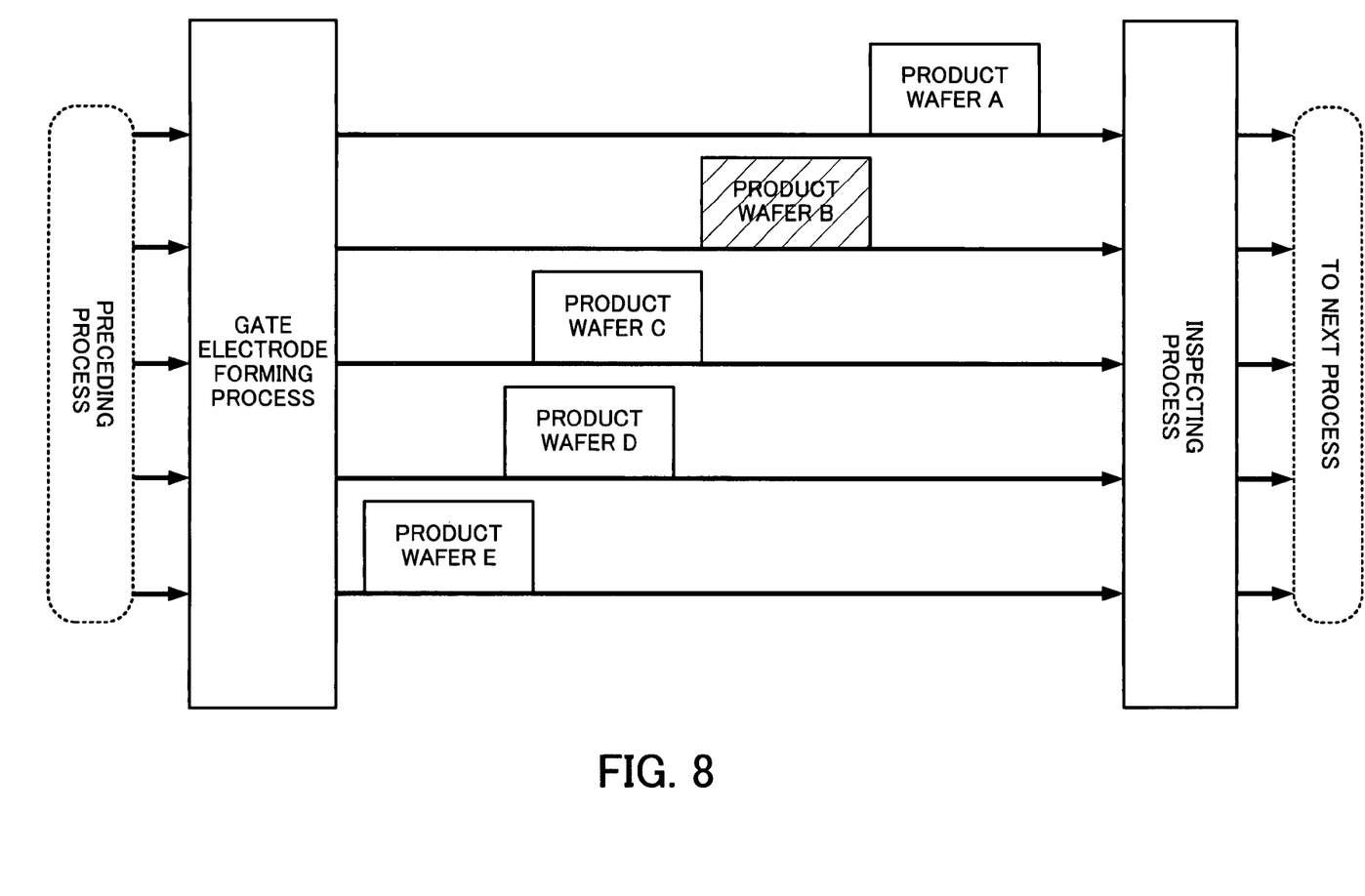
FIG. 8 is a diagram illustrative of an inspecting process as it is applied to a fabrication process.
Figure 9:
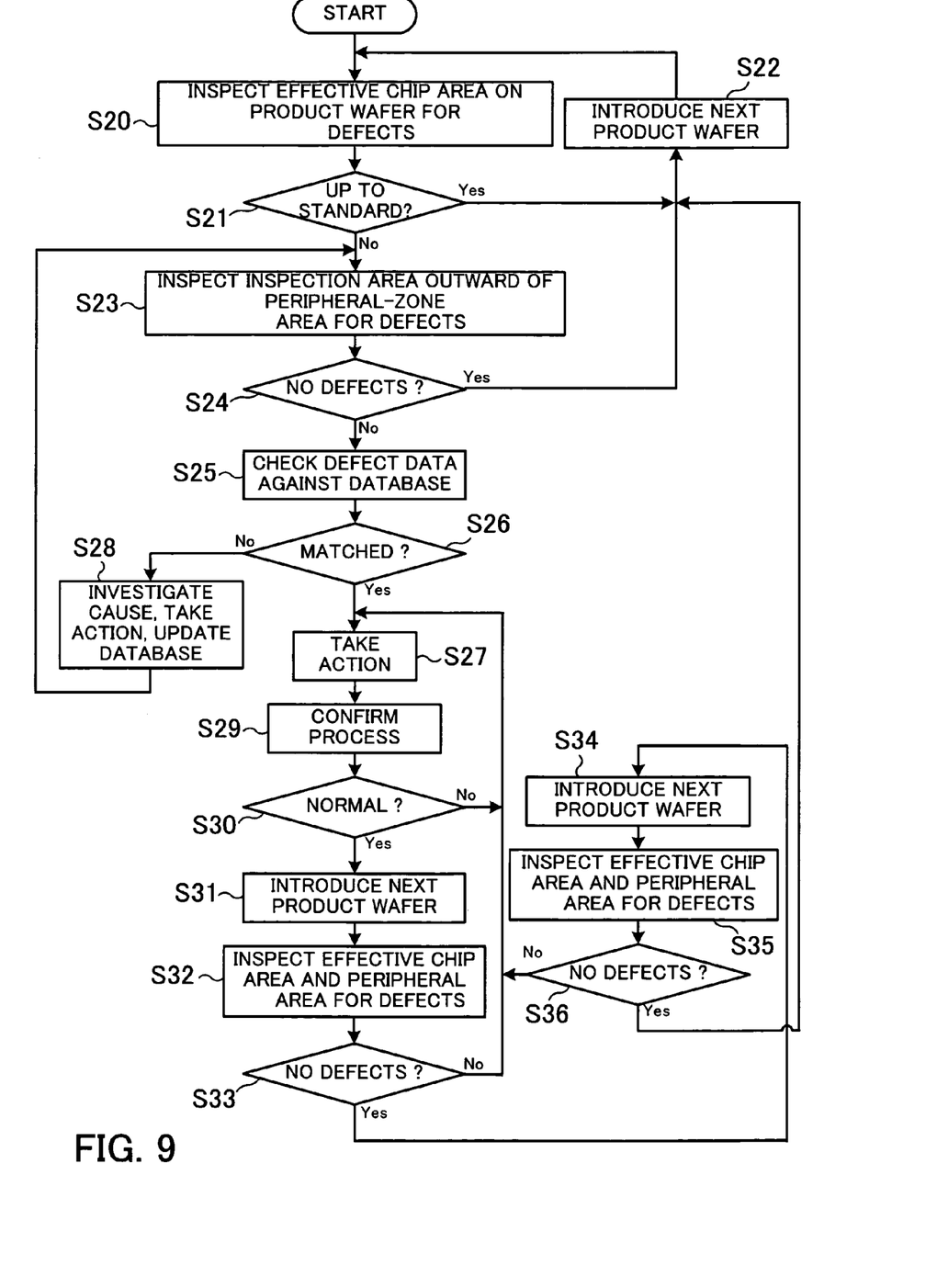
FIG. 9 is a flowchart of a manufacturing sequence of the fabrication process incorporating the inspecting process.

FIG. 8 is a conceptual diagram showing the wafer inspecting process as it is applied to a fabrication process. FIG. 9 is a flowchart of a manufacturing sequence of the wafer inspecting process as it is applied to the fabrication process.

In a factory, wafers (hereinafter referred to as "product wafers") on which chips for use as various products are formed flow along parallel production lines, respectively. In FIG. 8, five product wafers A, B, C, D, E, for example, are conceptually shown as flowing along the respective production lines. Each of the product wafers A, B, C, D, E is inspected by the above inspecting apparatus after it has been processed by a certain process, e.g., after it has been processed by the gate electrode forming process following the gate insulating film forming process. In FIG. 8, the product wafers A, B, C, D, E are fed successively in the order named to the inspecting process. After being inspected, the product wafers A, B, C, D, E are fed to a next process, i.e., the source/drain area forming process.

It is assumed that of the product wafers A, B, C, D, E, the product wafer B from the gate electrode forming process is suffering a non-standard defect. An overall flow of the MOS transistor fabrication process including the inspecting process will be described below with reference to FIGS. 8 and 9.

With respect to the product wafer A which has been processed by the gate electrode forming process and has initially been fed to the inspecting apparatus, the inspecting apparatus performs a defect inspection (first defect inspection) on only the effective chip area thereof (step S20) according to the processing sequence shown in FIG. 7 (steps S10 through S13), for example. Based on the defect inspection, a defect density $D_0$ of the entire effective chip area and a defect density $D_{0p}$ of each of the peripheral-zone chips in the effective chip area are calculated. Then, the calculated defect densities $D_0$, $D_{0p}$ are compared with a predetermined standard defect density value.

For the gate electrode forming process, the standard defect density value for defects, each having a size of 0.2 μm or greater, after a gate electrode material such as polysilicon or the like has been patterned, is preset as a range from 1/cm$^2$ to 3/cm$^2$ in a bright field and a range from 0.5/cm$^2$ to 1.0/cm$^2$, for example.

If the calculated defect density $D_0$ is within the standard defect range (Yes in step S21), then the product wafer B to be inspected next is fed to the inspecting process (step S22), and is processed according to the processing from step S20.

When the product wafer B from the gate electrode forming process is introduced into the inspecting apparatus, like the product wafer A, the inspecting apparatus performs the defect inspection (first defect inspection) on only the effective chip area thereof (step S20). Then, defect densities $D_0$, $D_{0p}$ are calculated and compared with the predetermined standard defect density value.

If the product wafer B is not up to the standard (No in step S21), then the inspecting apparatus ranks the calculated defect densities $D_{0p}$, selects a peripheral-zone chip based on the ranking, selects an inspection area such as a sectorial or arcuate inspection area or a hypothetical chip that is positioned in the peripheral area outside and near the selected peripheral-zone chip, and performs a defect inspection (second defect inspection) on the selected inspection area (step S23) according to the processing sequence (steps S14 through S18) shown in FIG. 7.

If no defect is found in the inspection area or a defect is found in the inspection area, but is in an allowable range as a result of the defect inspection in step S23 (Yes in step S24), then the product wafer C to be inspected next is fed to the inspecting process (step S22), and is processed according to the processing from step S20.

If a defect is found in the inspection area and the found defect is beyond the allowable range as a result of the defect inspection in step S23 (No in step S24), then before the product wafer C is introduced, the data of the defect is checked against a database of information about defects in the past (details of the found effects (the number of the defects, the sizes of the defects, the positions of the defects on the wafer, etc.), the fabrication apparatus which has produced the defects, and the operating conditions of the fabrication apparatus) (step S25).

The database may be provided in the inspecting apparatus or another apparatus. If the database is provided in another apparatus, then the inspection data acquired by the inspecting apparatus may be read into the other apparatus and checked against the information stored in the database.

If the database contains information that matches the inspection data (Yes in step S26) and the cause of the defects is discovered, then a suitable action is taken to eliminate the cause of the defects (step S27). For example, process conditions of the gate electrode forming process are changed, or a defective component of the fabrication apparatus is repaired.

If the database contains no information that matches the inspection data (No in step S26), then the engineer investigates the cause of the defects and a suitable action is taken (step S28), after which control goes back to step S23 to inspect the product wafer C again. In step S28, the information of the defects which is obtained by the investigation is newly added to the database, thereby updating the database.

After step S27, a bare wafer is used to confirm whether the gate electrode forming process is carried out properly or not (step S29). If it is determined that the gate electrode forming process is carried out properly (Yes in step S30), then the product wafer C to be inspected next is fed to the inspecting apparatus (step S31). If it is determined that the gate electrode forming process is not carried out properly (No in step S30), then control goes back to step S27 in which a suitable action is taken again.

If it is determined that the gate electrode forming process is carried out properly (Yes in step S30) and the next product wafer C is fed to the inspecting apparatus (step S31), then the inspecting apparatus performs a defect inspection (third defect inspection) on the product wafer C (step S32). According to this defect inspection, unlike the product wafers A, B, the product wafer C is inspected for defects in the effective chip area, and also inspected for defects in an inspection area such as a sectorial or arcuate inspection area or a hypothetical chip that is positioned in the peripheral area. In this manner, the stability of the gate electrode forming process after the product wafer inspection has been resumed is confirmed.

When the product wafer C is inspected for defects in the effective chip area and in an inspection area of a predetermined shape in the peripheral area, the entire peripheral area may be inspected, or only the same inspection area as the inspection area where defects were found on the preceding product wafer B may be inspected.

If no defects beyond the allowable range are found in both the effective chip area and the peripheral area of the product wafer C (Yes in step S33), then the product wafer D to be inspected next is fed to the inspecting apparatus (step S34), then the inspecting apparatus performs a defect inspection (third defect inspection) on the product wafer D for defects in both the effective chip area and the peripheral area thereof (step S35), like the product wafer C. If no defects beyond the allowable range are found on the product wafer D (Yes in step S36), then the product wafer E to be inspected next is fed to the inspecting apparatus (step S22), and is processed according to the processing from step S20.

Specifically, like the product wafer A, the inspecting apparatus performs a defect inspection (fourth defect inspection) on the product wafer E for defects in the effective chip area. Only if the effective chip area is not up to the standards and many defects are contained in a peripheral-zone chip in the effective chip area, then the inspecting apparatus performs a defect inspection (fifth defect inspection) on an area in the peripheral area which is located outward of the peripheral-zone chip.

If a defect beyond the allowable range is found on the product wafer D according to the defect inspection in steps S32, S35 (No in steps S33, S36), then control goes back to step S27 in which a suitable action is taken to eliminate the cause of the defect.

As described above, usually, a product wafer is inspected for defects only in the effective chip area. Only when a defect beyond the allowable range is found, an area in the peripheral area which is close to the defect is inspected for defects to investigate the source or cause of the defect. If necessary, a suitable action is taken to adjust process conditions or the fabrication apparatus. Subsequent product wafers are inspected for defects in both the effective chip area and the peripheral area in order to confirm the stability of the fabrication process. If the stability of the fabrication process is confirmed for the subsequent product wafers, then a next product wafer is inspected for defects only in the effective chip area.

When the fabrication process including the inspecting process is performed as described above, the time required by the inspecting process is shortened, and the yield of products can be increased without sacrificing the reliability of the inspecting process.

In the above embodiment, after the defective product wafer B has been processed, the two product wafers C, D are inspected for defects in both the effective chip area and the peripheral area in order to confirm the stability of the fabrication process. However, the illustrated sequence details are given by way of example only, and other sequence details may be employed. For example, only the product wafer C may be inspected for defects in both the effective chip area and the peripheral area in order, and if the stability of the fabrication process is confirmed for the product wafer C, the next product wafer D and subsequent product wafers may be inspected for defects only in the effective chip area.

According to the present invention, the effective chip area of a wafer is inspected for defects according to the first defect inspection, and an area in the peripheral area which is disposed outward of a peripheral-zone chip 2a which is selected based on the defect density calculated based on the results of the first defect inspection is inspected for defects according to the second defect inspection. This inspecting process allows highly reliable semiconductor devices to be produced efficiently, and is effective to increase the yield of semiconductor devices.

The foregoing is considered as illustrative only of the principles of the present invention. Further, since numerous modification and changes will readily occur to those skilled in the art, it is not desired to limit the invention to the exact construction and applications shown and described, and accordingly, all suitable modifications and equivalents may be regarded as falling within the scope of the invention in the appended claims and their equivalents.

What is claimed is:

1. A method of inspecting a wafer for defects, the wafer having a chip area and a peripheral area outward of said chip area, said method comprising the steps of:
 (a) performing a first defect inspection on said chip area;
 (b) calculating defect densities of peripheral-zone chips in said chip area which are close to said peripheral area, based on said first defect inspection;
 (c) selecting one of said peripheral-zone chips based on the calculated defect density; and
 (d) performing a second defect inspection on an area in said peripheral area which is positioned outward of the selected peripheral-zone chip.

2. The method according to claim 1, wherein said step (c) comprises the step of:
 selecting one of peripheral-zone chips whose defect density is greater than a predetermined value.

3. The method according to claim 1, further comprising the steps of:
 after said step (a) and before said step (b), calculating an overall defect density of said chip area based on said first defect inspection; and
 wherein said step (c) comprises the step of:
 selecting one of peripheral-zone chips whose defect density is greater than the calculated overall defect density of said chip area.

4. The method according to claim 1, wherein said step (d) comprises the steps of:
 establishing an inspection area of a predetermined shape in said peripheral area which is positioned outward of the selected peripheral-zone chip; and
 performing said second defect inspection on said inspection area.

5. The method according to claim 4, wherein said inspection area comprises a sectorial or arcuate area including an arcuate edge as a portion of an outer circumferential edge of said wafer.

6. The method according to claim 4, wherein said inspection area comprises a hypothetical chip disposed in said peripheral area of said wafer.

7. An apparatus for inspecting a wafer for defects, the wafer having a chip area and a peripheral area outward of said chip area, said apparatus comprising:
 first inspecting means for performing a first defect inspection on said chip area;
 calculating means for calculating defect densities of peripheral-zone chips in said chip area which are close to said peripheral area, based on said first defect inspection;
 selecting means for selecting one of said peripheral-zone chips based on the calculated defect density; and
 second inspecting means for performing a second defect inspection on an area in said peripheral area which is positioned outward of the selected peripheral-zone chip.

8. The apparatus according to claim 7, wherein said selecting means selects one of peripheral-zone chips whose defect density is greater than a predetermined value.

9. The apparatus according to claim 7, further comprising:
 means for an overall defect density of said chip area based on said first defect inspection; and
 wherein said selecting means selects one of peripheral-zone chips whose defect density is greater than the calculated overall defect density of said chip area.

10. The apparatus according to claim 7, wherein said second inspecting means establishes an inspection area of a predetermined shape in said peripheral area which is positioned outward of the selected peripheral-zone chip, and performs said second defect inspection on said inspection area.

11. The apparatus according to claim 10, wherein said inspection area comprises a sectorial or arcuate area including an arcuate edge as a portion of an outer circumferential edge of said wafer.

12. An apparatus according to claim 10, wherein said inspection area comprises a hypothetical chip disposed in said peripheral area of said wafer.

13. A method of manufacturing a semiconductor device from a wafer having a chip area and a peripheral area outward of said chip area, said method comprising the steps of:
 (a) performing a first defect inspection on said chip area;
 (b) calculating defect densities of peripheral-zone chips in said chip area which are close to said peripheral area, based on said first defect inspection;
 (c) selecting one of said peripheral-zone chips based on the calculated defect density; and
 (d) performing a second defect inspection on an area in said peripheral area which is positioned outward of the selected peripheral-zone chip.

14. The method according to claim 13, said step (d) comprises the steps of:
 establishing an inspection area of a predetermined shape in said peripheral area which is positioned outward of the selected peripheral-zone chip; and
 performing said second defect inspection on said inspection area.

15. The method according to claim 14, wherein said inspection area comprises a sectorial or arcuate area including an arcuate edge as a portion of an outer circumferential edge of said wafer.

16. The method according to claim 14, wherein said inspection area comprises a hypothetical chip disposed in said peripheral area of said wafer.

17. The method according to claim 13, further comprising the steps of:
 (e) after said step (d), performing a necessary action on a process by which said wafer has been processed prior to said step (a); and
 (f) performing a third defect inspection on the chip area and the peripheral area outward of said chip area of a next wafer which has been processed by said process on which said necessary action has been performed.

18. The method according to claim 17, further comprising the steps of:
 after said step (f), if the stability of said process is confirmed based on said third defect inspection, performing a fourth defect inspection on the chip area of a further next wafer which has been processed by said process subsequently to said next wafer;
 calculating a defect density of a peripheral-zone chip which is located closely to the peripheral area outward of said chip area of said further next wafer, among chips in said chip area of said further next wafer, based on said fourth defect inspection; and
 performing a fifth defect inspection on the peripheral area of said further next area only if the calculated defect density of the peripheral-zone chip on said further next wafer is greater than a predetermined value.

* * * * *